United States Patent

Clamroth et al.

[11] 4,181,023
[45] Jan. 1, 1980

[54] APPARATUS FOR SHORT-DURATION TESTS FOR DETERMINING THE FLOWABILITY OF POWDERS

[75] Inventors: Rudolf Clamroth; Hans Loske, both of Leverkusen; Jochen Schnetger, Odenthal-Hoeffe, all of Fed. Rep. of Germany

[73] Assignee: Bayer Aktiengesellschaft, Leverkusen, Fed. Rep. of Germany

[21] Appl. No.: 914,816

[22] Filed: Jun. 12, 1978

[30] Foreign Application Priority Data

Jun. 29, 1977 [DE] Fed. Rep. of Germany ....... 2729252

[51] Int. Cl.² .............................................. G01N 33/00
[52] U.S. Cl. ..................................... 73/432 R; 73/59
[58] Field of Search .......................... 73/59, 432 R, 60

[56] References Cited

U.S. PATENT DOCUMENTS

| | | |
|---|---|---|
| 2,382,979 | 8/1945 | Demb ................................. 73/59 |
| 2,410,385 | 10/1946 | Loukomosky ........................... 73/59 |
| 2,633,027 | 3/1953 | Bunnel ............................. 73/432 R |
| 3,538,758 | 11/1970 | Karper ................................. 73/59 |
| 3,581,558 | 6/1971 | Porter ................................. 73/59 |

OTHER PUBLICATIONS

Brochure of C. W. Brabender Instruments Inc., #400--1-60; Visco-Corder.

*Primary Examiner*—S. Clement Swisher
*Assistant Examiner*—Denis E. Corr
*Attorney, Agent, or Firm*—Sprung, Felfe, Horn, Lynch & Kramer

[57] ABSTRACT

For the short-duration determination of the flowability of rubber powder after storage, the rubber powder is poured into a cylindrical container in which is immersed a resistance element. This element displays an analogue value via a torque measuring device when there is relative rotation between the container and the resistance element.

7 Claims, 6 Drawing Figures

APPARATUS FOR SHORT-DURATION TESTS FOR DETERMINING THE FLOWABILITY OF POWDERS

The invention relates to an apparatus for short-duration tests for determining the flowability of powders under storage conditions. Rubber powders which are stored in bags or silos for prolonged periods, in particular under elevated pressure and/or at undesirable temperatures, lose some of their flowability so that it is more difficult to empty the bags or silos. It is therefore important in practice to have reliable advance information as to their subsequent flowability.

In the past, a testing instrument according to the American Society for Testing Materials was used for carbon block. A defined volume of 325 cm$^3$ of the powder was compressed in a cylinder for ten minutes by a standardised testing method. After releasing the pressure, the base of the cylinder was removed and the powder was observed to see whether it flows out. A bridge was formed by high pressure forces so that some of the powder remained in the cylinder. The greatest pressure at which a bridge was not yet formed is formed by increasing the load in stages of 5 lbs.

A disadvantage of this method is that there is slight differentiation and, moreover, no means of determination for powders which flow well and which form bridges at forces of pressure above 30 lbs. This method is quite important in the carbon black industry but is poorly related to practice in the case of rubber powder. In addition, this method is not independent of the bulk density. At lower bulk density, values which are too small and which do not comply with practice are measured.

Attempts have been made to determine the flowability from a combination of properties in the Japanese Hosakawa testing method. The angle of repose is a significant quantity which is produced from the angle between the conical surface of a cone of powder formed by pouring the powder on to a level base and the base itself. The flowability is then determined with the aid of other parameters.

This method is very complicated and troublesome. The results found are differentiated too little for rubber powder and do not comply well with practical requirements.

In another method, the run-out time from a hopper is measured. This method depends substantially upon the bulk density, does not give sufficient differentiation in the measured result for rubber powder, and so is unsuitable for predictions in practice.

The Schwedes-Jenicke method is also known in which a measuring beaker is composed of rings which are filled with powder and are off-set with respect to each other by a translational motion. With this method, the force required for shearing off the powder is measured. This method is only used for fundamental scientific investigations as it demands very accurate adjustments. Since the displacement of the concentric ring only provides usable results over a short path, it is suitable only for detecting the startg force.

Peschl uses the same arrangement as Schwedes-Jenicke but he rotates a cover by means of which the powder is compacted against a pot. The torque required for rotating the cover is a measure of the flowability. This method does not give sufficient differentiation of the measured result for rubber powder. In addition, it is necessary to position the cover accurately in relation to the pot, otherwise the results are falsified by unreproducible frictional forces.

An object of the invention is to provide a testing apparatus which allows reliable prediction of the flowability of powders, particularly rubber powder, in a relatively short period (from 1 to 1440 minutes), under storage conditions, wherein the quantities measured in determining the flowability are obtainable by means of simple measuring means suitable for routine examinations.

According to the invention there is provided an apparatus for determining the flowability of powders under storage conditions comprising a cylindrical beaker open at the top for receiving a sample of the said powder, the beaker being arranged in upright fashion, at least one or more loading plates of predetermined weight introducible from above in order to compress powder uniformly, means for rotating the beaker, a resistance element insertable centrally into the powder in the beaker, and a torque measuring device for measuring the torque on the resistance element when the beaker rotates.

It was surprising for the skilled man that pre-compaction of the rubber powder with particle sizes of from 0.1 to 1 mm over a maximum of 24 hours in a cylindrical beaker loaded from above by weights and measurement of a torque angle with a resistance element lowered from above into the compacted and thus stirred powder with slow rotation of the beaker at from 1 to 2 revolutions per minute are sufficient to obtain good reproducibility and to make reliable assertions about suitability for storage which are closely related to practice.

It is particularly advantageous that the apparatus is suitable for routine examination because the apparatus may be used without further adjustment after determining the reference points. It is simple to manage, and the risk of servicing errors is low. The cost of the time tests is relatively low as beakers and weights are inexpensive and the expensive measuring instrument is required for a short period only at the end.

The method is flexible as the resistance elements may be exchanged, the speed of rotation may be altered and the weight of the load may be adapted so that optimum measuring conditions may be regulated in each case.

In one embodiment, from 4 to 8 axially parallel vanes equiangularly offset from one another are arranged about an axis.

A defined shearing body is formed in the powder by the 4 to 8-vaned resistance elements and this defined shearing body is twisted by the rotating surrounding powder in such a way that the torque angle may be measured precisely under constant conditions.

The lower rim of the resistance element is designed as a cutting edge in a particular embodiment. Disturbances in the texture of the compacted rubber powder are kept as low as possible by the sharp cutting edges on the lower rim of the resistance element and this promotes accuracy of measurement.

In another embodiment, a heat exchanger is provided above the beaker and/or the loading plates. Temperature regulation has the advantage of allowing the flowability to be tested after or during certain temperatures in the short-duration test.

An embodiment of the invention is shown in the accompanying drawings in which

Figures 1, 2:
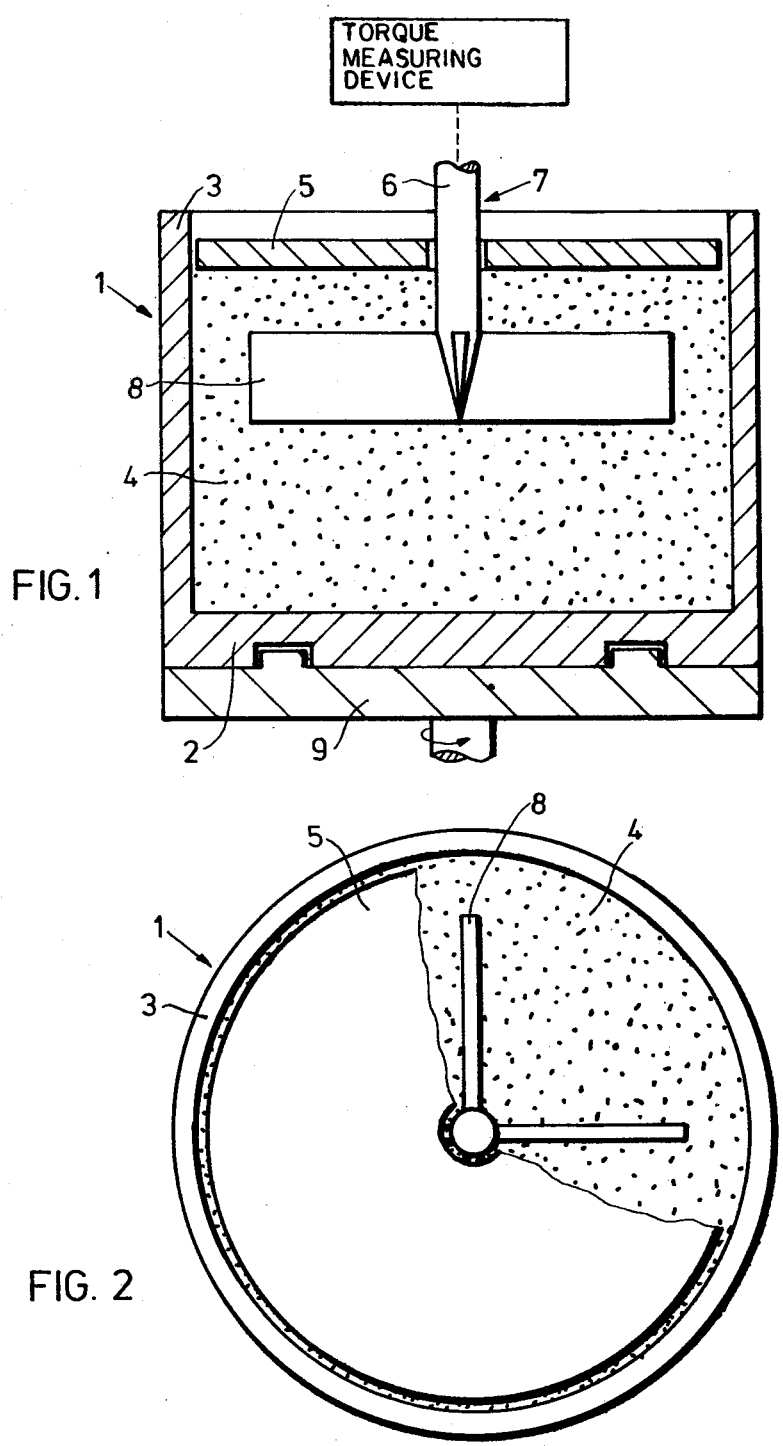
FIG. 1 is a section through a beaker with an immersed resistance element.
FIG. 2 is a plan view of a beaker, partially in section.

FIGS. 1 and 2 show an upright cylindrical beaker 1 with a base 2 and side walls 3 filled with powder 4. A loading plate 5 through which passes a shaft 6 of a resistance element 7 rests on the powder. The resistance element has four axially parallel vanes 8 positioned in the powder at its lower end. The beaker 1 is located on a rotating table 9.

Figure 3:
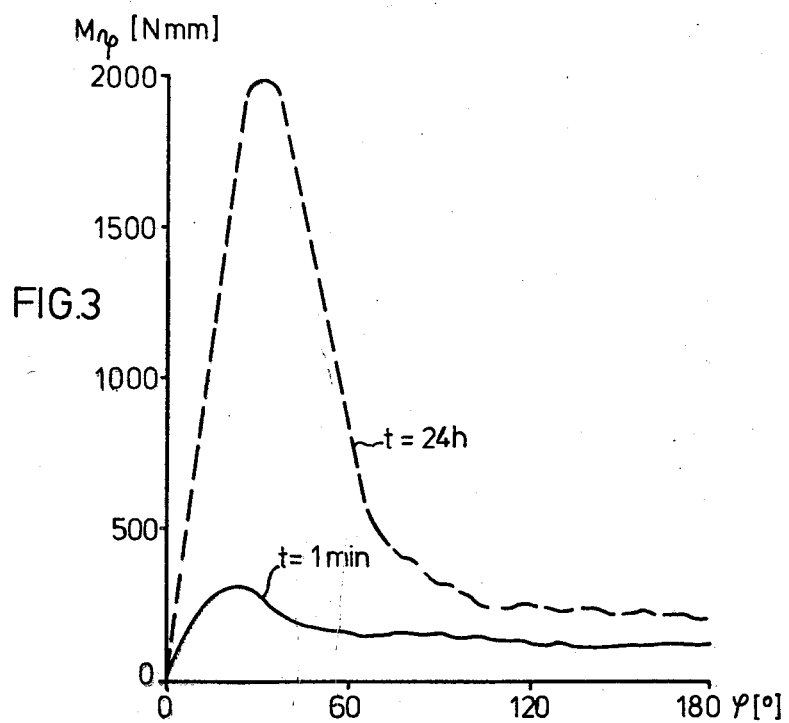
FIGS. 3 and 4 are graphs showing the torque as a function of the angle of rotation for various powders.
Figure 4:
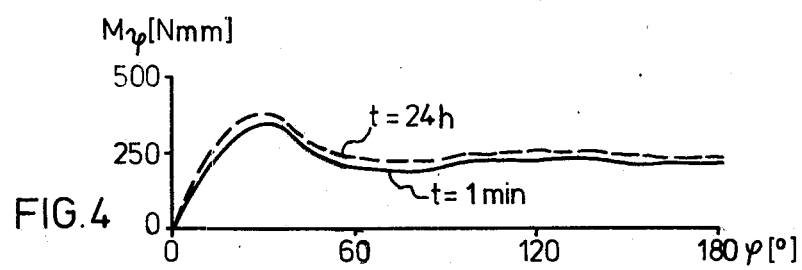

FIGS. 3 and 4 are graphs each showing, for a different rubber powder, the torque M as a function of the angle of rotation $\phi$.

Figure 5:
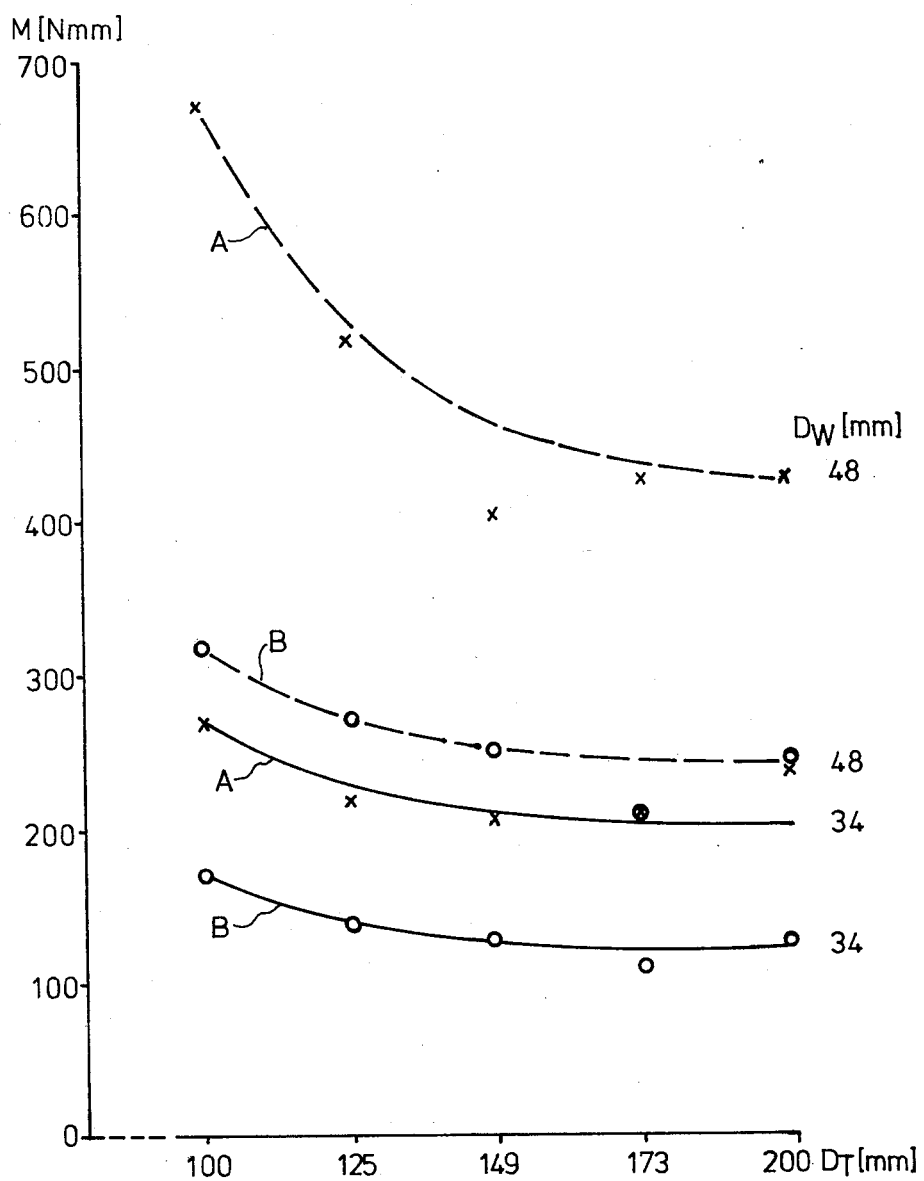
FIG. 5 is a graph showing the torque as a function of the diameter of the beaker and the diameter of the resistance element.

FIG. 5 shows the dependence of the torque M on the beaker diameters $D_T$ for various values of the diameter $D_W$ of a four-vaned resistance element, for two different rubber powders.

Figure 6:
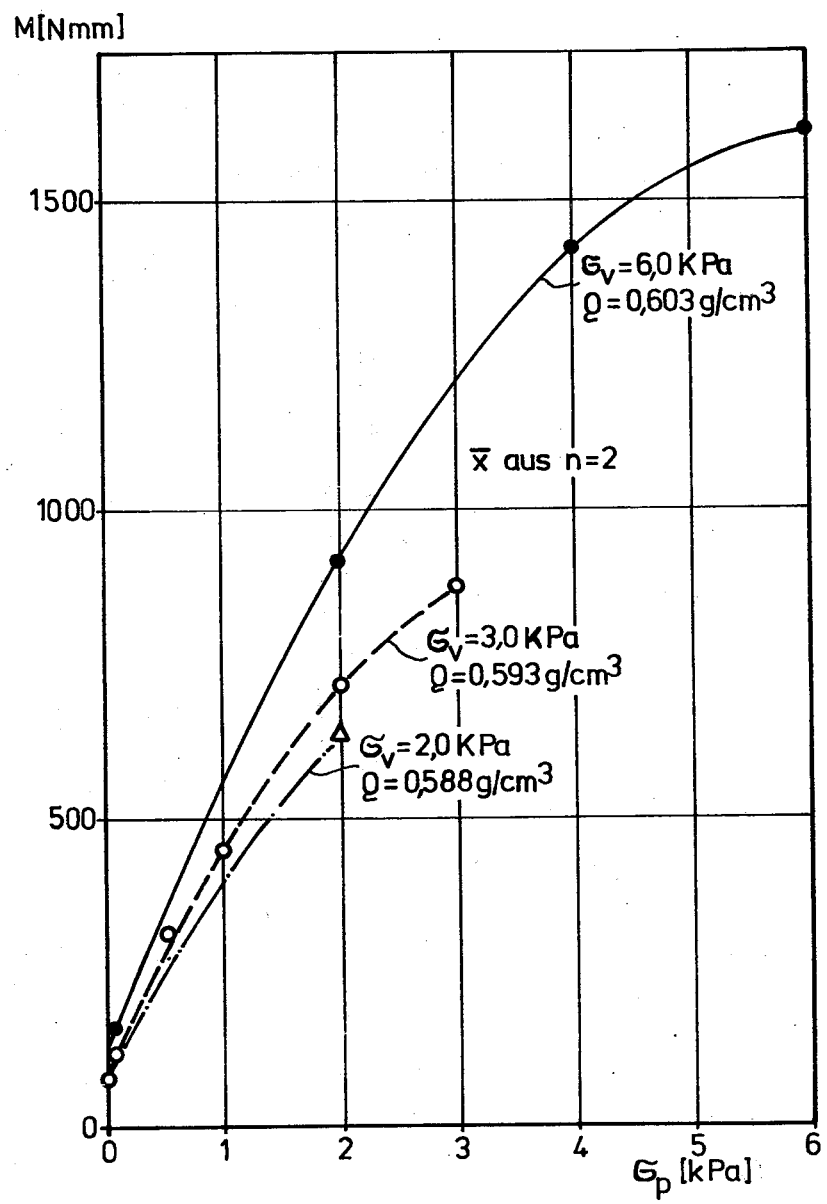
FIG. 6 is a graph showing the torque as a function of test tensions at various initial compressions.

FIG. 6 shows the torque M as a function of the test tension $\theta_p$ for various compressions $\theta_v$, which have acted for 5 minutes in each case.

When testing the suitability for storage, the following steps are carried out. The beaker is filled with the powder to be measured in such a way that a feeding cone is formed above the upper rim. The powder heaped up above the upper rim is stripped off by a straight-edged ruler. The powder remaining in the beaker is weighed and gives the bulk density $\rho_s$ (see also DIN 53 486). The loading plates are placed on the powder which is compressed to a specific initial compression $\theta_v$. The duration of loading may be varied; durations of 1 minute and 24 hours were stipulated in this case. With short loading periods, the beaker is placed on the rotating table before-hand and the resistance element is introduced. With longer loading periods, this process is carried out after pre-loading.

The test load is applied and is smaller or equal to the pre-loading. The compression then remains and corresponds to the pre-loading $\theta_v$.

The beaker is rotated slowly by the rotating table. The torque M required for twisting the resistance element in the powder is registered on a recorder as a function of the angle of rotation $\phi$, as shown in FIGS. 3 and 4.

The test is carried out after 1 minute and after 24 hours pre-loading. The quotient $M_{24h}/M_{1\,min}$ is formed from the maximum torques found and is correlated with the practical requirements of rubber powder in the following manner.

| | |
|---|---|
| <2 | very good |
| 2 to 4 | good |
| 4 to 6 | satisfactory |
| >6 | unsatisfactory |

EXAMPLE 1
(FIG. 3)

A powder composed of nitrile butadiene rubber with 33% acrylonitrile content, a Mooney viscosity of 55 Mooney units (ML 4 according to DIN 52 523) and an average particle diameter of 0.6 mm was tested.

| | |
|---|---|
| Diameter of beaker | 100 mm |
| Diameter of four-vaned resistance element | 48 mm |
| Height of four-vaned resistance element | 15 mm |
| Height of filling | 110 mm |
| Depth of immersion | 10 mm |
| Speed of rotating table | 1.5 1/min. |
| Loading time t | 1 min./24 h |
| Initial compression $\sigma_v$ | 2.4 kPa |
| Test compression $\sigma_p$ | 1.3 kPa |

Result: The quotient of the two maximum values is given by:

$$Q = 2000/320 = 6.2$$

Suitability for storage is not satisfactory since the value of the quotient and the distance between the two curves is relatively large.

EXAMPLE 2
(FIG. 4)

A powder composed of chloroprene rubber having a Mooney viscosity of 103 Mooney units (ML 4 according to DIN 53 523) and an average particle diameter of 0.9 mm was tested.

| | |
|---|---|
| Diameter of beaker | 100 mm |
| Diameter of four-vaned resistance element | 48 mm |
| Height of four-vaned resistance element | 15 mm |
| Height of filling | 110 mm |
| Depth of immersion | 10 mm |
| Speed of rotating table | 1.5 min$^{-1}$ |
| Loading time t | 1 min./24 h |
| Initial compression $\sigma_v$ | 2.4 kPa |
| Test compression $\sigma_p$ | 1.3 kPa |

Result: The quotient of the two maximum values is given by:

$$Q = 420/380 = 1.1$$

The suitability for storage is very good since the curves run close together.

What we claim is:

1. An apparatus for determining the flowability of powders under storage conditions comprising a cylindrical beaker open at the top for receiving a sample of the powder to be tested and a base for enabling the beaker to be disposed in an upright position, at least one loading plate of predetermined weight introducible through the open top to uniformly compress powder received in the beaker, means for rotating the beaker, a sharp resistance element configured to centrally slice into the powder in the beaker after compression by the plate with the powder then being otherwise free of disturbance, and a torque measuring device for measuring the torque on the resistance element when subsequently the beaker rotates.

2. An apparatus according to claim 1, wherein said means for rotating the beaker comprises a rotatable table on which the beaker is positionable in an upright manner.

3. An apparatus according to claim 1, wherein the resistance element comprises a shaft and from four to eight plates equiangular spaced from one another about the shaft, wherein the lower edge of each plate is a cutting edge.

4. An apparatus according to claim 3, wherein the loading plate has an aperture in the central portion thereof and the shaft is insertable through the loading plate with the plates disposed therebelow.

5. A method for determining the flowability of powders under storage conditions comprising:
 a. introducing powder to be tested into an open top beaker;
 b. precompressing the powder to an initial compression by applying a first load for a first time period.
 c. inserting a resistance element centrally into the powder in the beaker;
 d. applying a test load which is not more than the first load;
 e. rotating the beaker and measuring the torque on the resistance element;
 f. removing the resistance element;
 g. precompressing the powder in an open top beaker to said initial compression for a second time period greater than the first time period;
 h. inserting said resistance element;
 i. applying said test load; and
 j. rotating the beaker and measuring the torque on the resistance element.

6. The method according to claim 5, wherein rubber powder having a particle size of from 0.1 to 1 mm is precompressed in step (g) for up to 24 hours.

7. The method according to claim 6, wherein the beaker is rotated in steps (e) and (j) at from 1 to 2 revolutions per minute.

* * * * *